United States Patent [19]

Haber et al.

[11] Patent Number: 4,919,657

[45] Date of Patent: Apr. 24, 1990

[54] DENTAL SYRINGE HAVING A MEDICATION FILLED CARPULE AND A RETRACTABLE NEEDLE CANNULA

[75] Inventors: Terry M. Haber, El Toro; Cark B. Foster, Laguna Niguel, both of Calif.

[73] Assignee: Habley Medical Technology Corporation, Laguna Hills, Calif.

[21] Appl. No.: 270,094

[22] Filed: Nov. 14, 1988

[51] Int. Cl.$^5$ ............................................. A61M 5/245
[52] U.S. Cl. ................................. 604/232; 604/234; 604/263; 604/197
[58] Field of Search ............... 604/110, 165, 121, 181, 604/182, 186, 187, 207, 210, 214, 218, 220, 232, 234, 235, 240–241, 139, 197–198, 263

[56] References Cited

U.S. PATENT DOCUMENTS

| | | | |
|---|---|---|---|
| 1,770,634 | 7/1930 | Smith | 604/234 |
| 2,994,323 | 8/1961 | Dann et al. | 604/232 |
| 3,605,744 | 9/1971 | Dwyer | 604/139 |
| 3,878,846 | 4/1975 | Rimbaud | 604/197 |
| 4,333,458 | 6/1982 | Margulies et al. | 604/232 |
| 4,702,738 | 10/1987 | Spencer | 604/263 |

Primary Examiner—Jerome L. Kruter
Assistant Examiner—Michael Rafa
Attorney, Agent, or Firm—Morland C. Fischer

[57] ABSTRACT

A reusable dental syringe including a conventional medication filled carpule and a conventional double ended needle cannula which is to be retracted into a compact enclosure to permit the safe handling and disposal of the cannula while avoiding an accidental needle stick and the possible spread of disease. The carpule is inserted into a hollow carpule adapter to engage a movable needle carrier at the distal end of the adapter. The combination carpule and adapter are loaded into the cylinder of the syringe, and the needle cannula is attached to the needle carrier to penetrate the carpule. At the conclusion of an injection, the combination carpule and carpule adapter are rotated outwardly from the syringe cylinder, and the carpule is then pulled rearwardly through the adapter, whereby to correspondingly relocate and anchor the movable needle carrier at the proximal end of the adapter. Accordingly, the needle cannula is retracted into and surrounded by the adapter so as to be irretrievably located and rendered non-reusable therewithin.

16 Claims, 5 Drawing Sheets

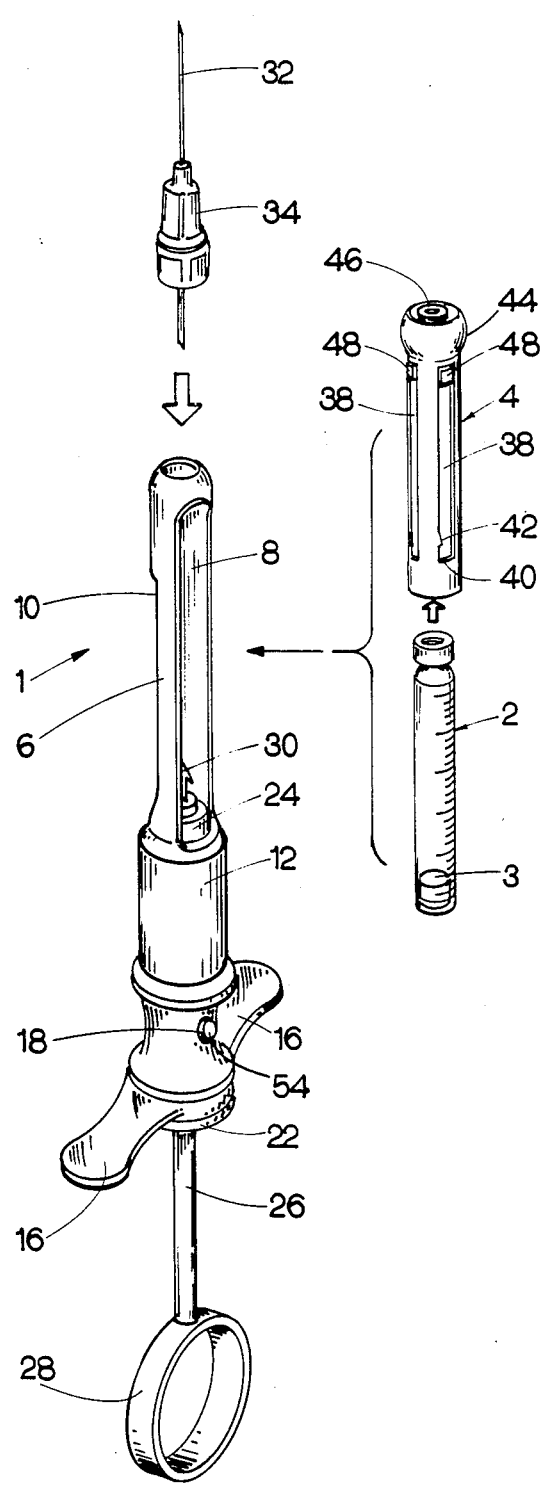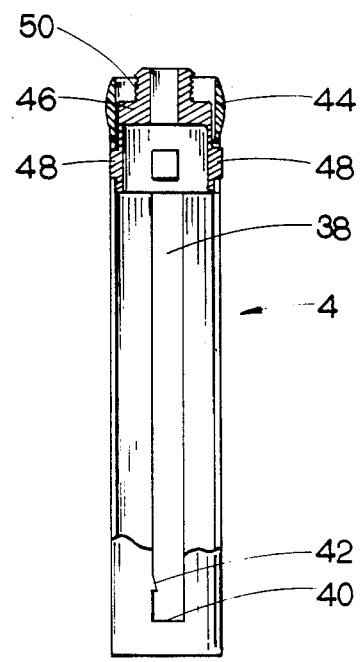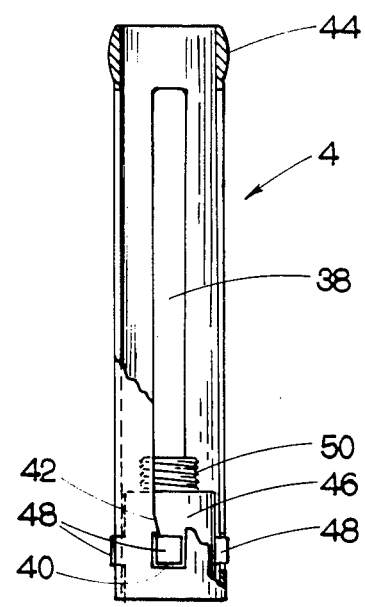

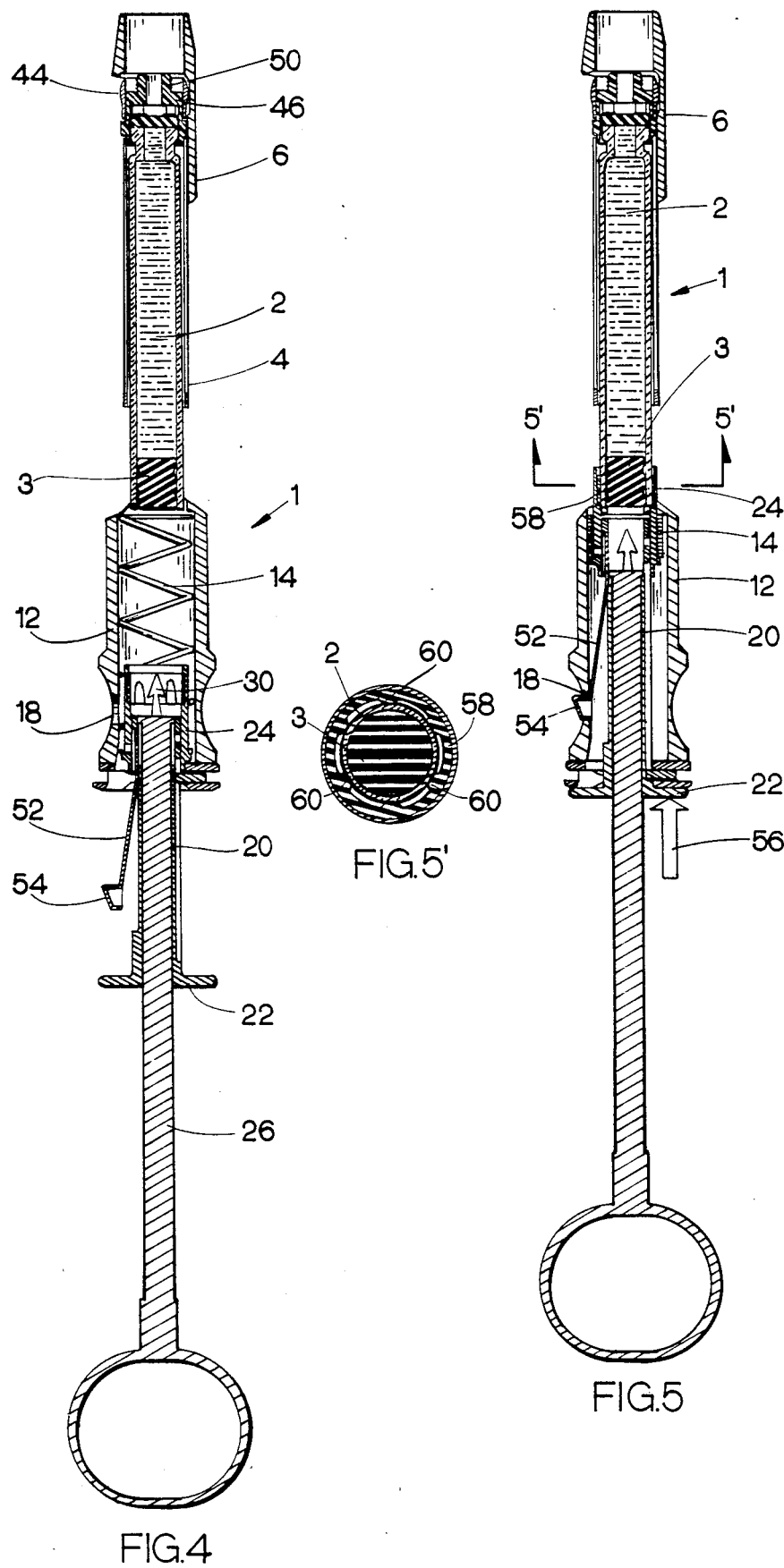

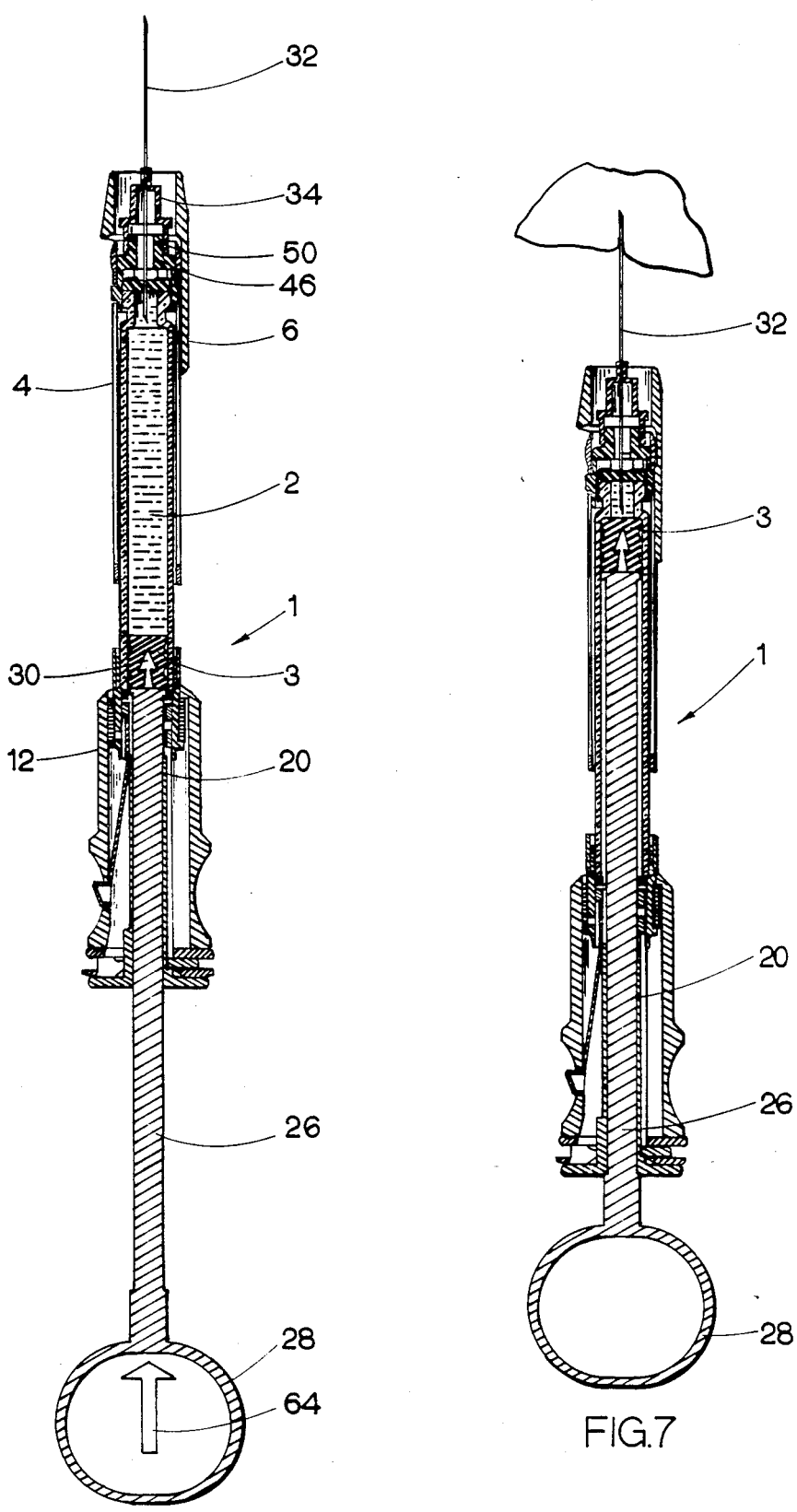

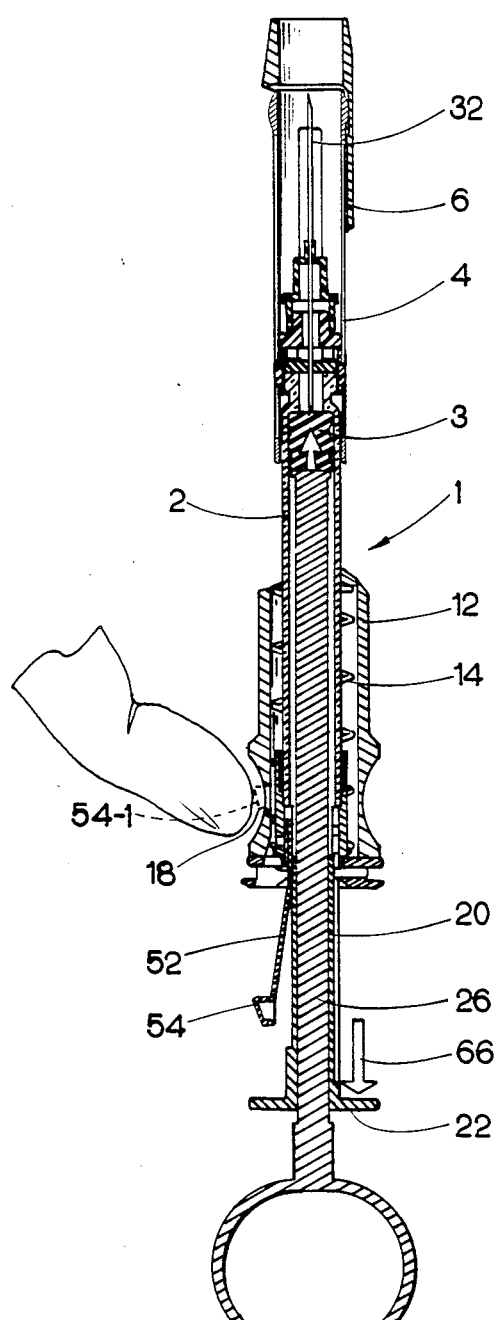
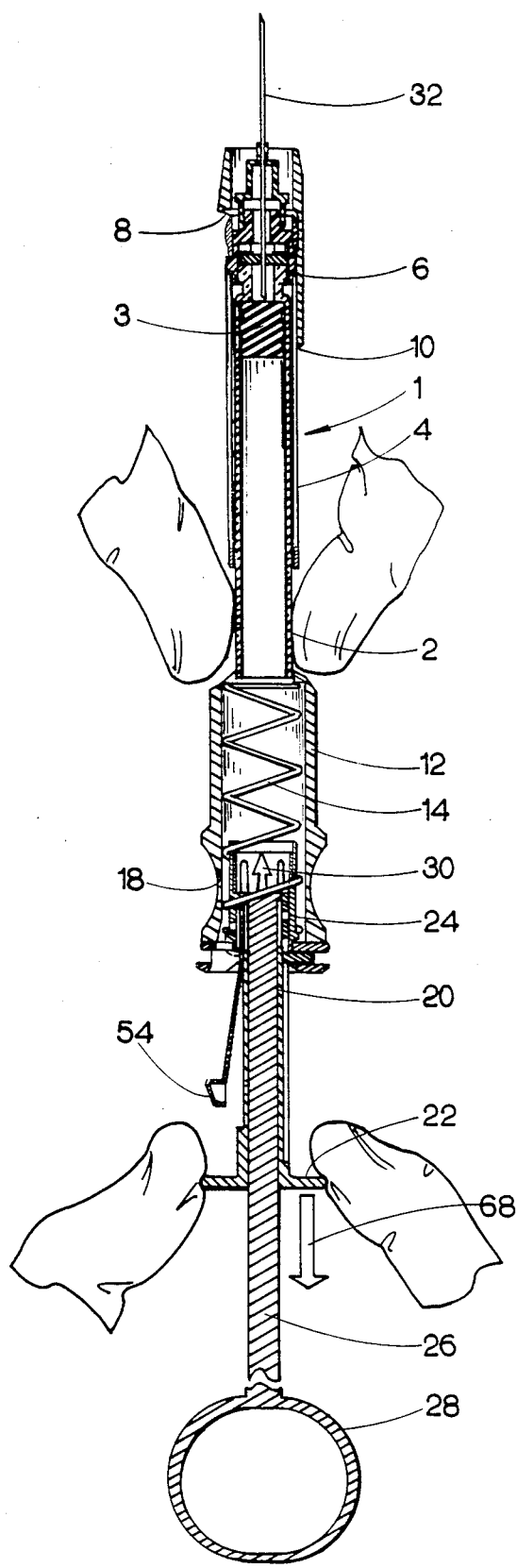
FIG.8
FIG.9

DENTAL SYRINGE HAVING A MEDICATION FILLED CARPULE AND A RETRACTABLE NEEDLE CANNULA

BACKGROUND OF THE INVENTION

1. FIELD OF THE INVENTION

This invention relates to a reusable, carpule based dental syringe having a double ended needle cannula which is to be retracted within a compact enclosure to permit the safe handling and disposal of the cannula while avoiding an accidental and possibly life threatening needle stick.

2. BACKGROUND ART

Dental syringes of the type having a pre-filled carpule of fluid medication and a double ended hypodermic needle cannula are well known in the art for injecting such medication from the carpule to a targeted tissue area of a patient. However, at the completion of the injection, the needed cannula is typically locked in an axially extended position projecting outwardly from a distal bore formed through the syringe cylinder.

In some cases, the syringe may be used to treat a patient having a communicable disease. Prior to disposing the syringe, the needle cannula is frequently broken or destroyed to prevent reuse. Dental office workers are especially susceptible to accidental and potentially infectious needle sticks due to the careless handling or breaking of the needle and disposing of the syringe after use. The resulting mini-accident caused by an accidental needle stick typically requires a blood test for such diseases as AIDS and hepatitis. The corresponding cost and inefficiency of testing dntal office workers who have received such an accidental needle stick result in considerable waste, which may be particularly damaging to a dental facility which is striving for economy.

The following U.S. patent and application, which have been or will be assigned to the assignee of the present invention disclose carpule based dental syringes having a retractable needle cannula and a flexible locking arm for controlling the movement of said carpule relative to the cylinder of the syringe: U.S. Pat. No. 4,767,413 issued Aug. 30, 1988 and U.S. Pat. Application No. 135,607 filed Dec. 21, 1987.

SUMMARY OF THE INVENTION

In general terms, a reusable dental syringe is disclosed including a hollow cyinder having open proximal and distal ends and an axially aligned hollow body portion. A conventional medication filled carpule is pushed through a hollow carpule adapter for receipt by a movable needle carrier at the distal end of the adapter, and the combination carpule and adapter are loaded into the cylinder through a longitudinally extending opening therein. A conventional hub supported, double ended needle cannula is attached to the needle carrier via the open distal end of the cylinder so as to penetrate the carpule and communicate with the interior thereof. A hollow control rod is advanced distally, against the bias of a helical compression spring, through the hollow body of the syringe and the open proximal end of the syringe cylinder so that a retaining sleeve at one end of the control rod will be correspondingly advanced into surrounding engagement with the proximal end of the carpule to prevent displacement of the carpule relative to the cylinder. A flexible spring arm, which carries a release button at one end thereof, is attached to and movable with the control rod until the release button pops through a hole in the syringe body to lock the control rod at its distally advanced position. A piston stem is slidable distally through the hollow control rod to be connected to and control the movement of a piston through the carpule so that medication may be expulsed from the carpule via the needle cannula.

In operation, the dentist locates the needle cannula at a targeted tissue area of the patient and slides the piston stem distally through the hollow control rod and into the carpule. The distal movement of the piston stem drives the piston through the carpule to administer an injection of the medication into the targeted tissue. Upon completing the injection, and while holding the carpule against axial displacement, the dentist presses the release button of the spring arm through the hole in the syringe body to release the control rod from its distally advanced position, whereby the formerly compressed spring is now free to return to the relaxed condition. The control rod and piston stem are then withdrawn rearwardly through the syringe body and away from the carpule, such that the retaining sleeve of the control rod is moved out of engagement with the carpule and the piston stem is disconnected from the piston.

The combination carpule and carpule adapter are rotated downwardly, around an enlarged end of the adapter, through the longtudinally extending opening in the syringe cylinder. Next, the dentist grasps and pulls the carpule rearwardly through the adapter to correspondingly relocate the movable needle carrier and the needle cannula attached thereto towards the proximal end of the adapter. The needle carrier is anchored in its relatively proximal position by means of locking detents located at the proximal end of the adapter to prevent any further displacement of the needle cannula. Accordingly, the needle cannula is retracted into and surrounded by the carpule adapter to form a safe and compact package which is suitable for disposal and in which the cannula is rendered irretrievable and non-reusable to thereby avoid an accidental needle stick and the possible spread of disease.

BRIEF DESCRIPTION OF THE DRAWINGS

FIG. 1 shows a partially exploded view of the dental syringe which forms the present invention;

FIGS. 2 and 3 show partial cross-sections of a carpule adapter which is to be interfaced with a conventional medication filled carpule and loaded into the cylinder of the dental syringe of FIG. 1;

FIG. 4 is a cross-section of the dental syringe in a pre-injection state;

FIGS. 5-7 are cross-sections of the dental syringe in an injection state where medication is expulsed from the carpule to a targeted tissue area via a conventional double ended needle cannula;

FIG. 5' is a cross-section taken along lines 5'-5' of FIG. 5;

FIG. 8 is a cross-section of the dental syringe which illustrates an optional step of temporarily retracting the needle cannula into the syringe cylinder if an injection is to be administered in step-wise increments;

FIG. 9 is a cross-section of the dental syringe in a post-injection state; and

DESCRIPTION OF THE PREFERRED EMBODIMENT

Figure 10:
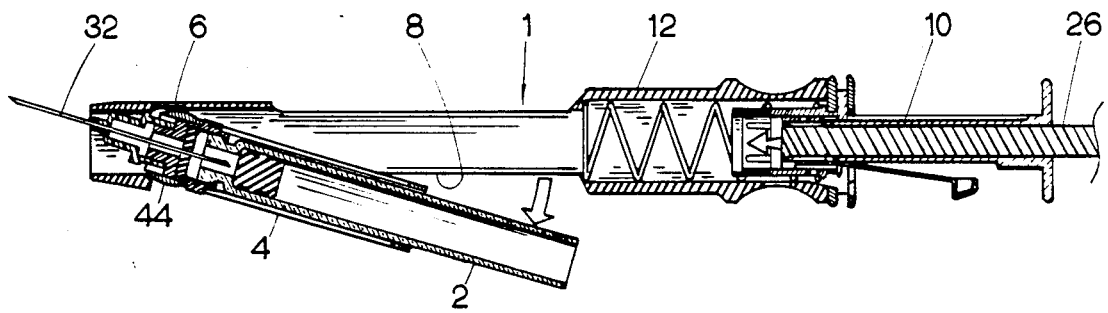
FIGS. 10-12 illustrate the retraction and anchoring of the needle cannula within the carpule adapter to form a compact package suitable for handling and disposal in which the cannula is rendered irretrievable and nonreusable.

The carpule based, reusable dental syringe 1 of the present invention is now described in detail while referring to the drawings, where FIG. 1 shows a partially exploded view of the syringe 1 and a combination carpule 2 and carpule adapter 4. Carpule 2, which is typically formed from glass or other transparent material, is of conventional design and includes a rubber piston 3 located at the proximal end thereof. Carpule 2 is filled with a supply of fluid medication, such as novacain, or the like. The details of carpule adapter 4 will be described when referring to FIGS. 2 and 3.

The syringe 1 includes a hollow cylinder or barrel 6 having open proximal and distal ends, a longitudinally extending opening 8 formed thorough one side of the cylinder (for removable receipt of the combination carpule 2 and adapter 4), and a longitudinally extending window 10 formed through the opposite side (for gaining visible access to the medication filled carpule when such carpule is loaded into the interior of hollow cylinder 6). Coextensively joined to and axially aligned with the cylinder 6 is a hollow body portion 12. Located within the body portion 12 of syringe 1 is a helical compression spring (designated 14 in FIG. 4). Projecting radially outward in opposite directions from the body portion 12 is a pair of finger ledges 16. A hole 18 (best illustrated in FIG. 4) is formed through one side of body portion 12 between the oppositely extending finger ledges 16. The purpose of hole 18 for receiving a spring biased button 54 therethrough will be described later when referring to FIG. 4

A hollow control rod (designated 20 in FIG. 4) is slidably received in and adapted for axial and reciprocal movement through the hollow body portion 12 of syringe 1. Affixed to one end of the control rod 20 is a disk-like arming flange 22. Affixed to the opposite end of control rod 20 is a hollow retaining sleeve 24. As will soon be explained, a force for moving the control rod 20 distally through hollow body portion 12 is applied to the arming flange 22, whereby to correspondingly advance retaining sleeve 24 (against the bias of compression spring 14) through the open proximal end of cylinder 6 for surrounding and engaging the proximal end of carpule 2. A flexible spring arm (designated 52 in FIG. 4) is attached to and movable with the control rod 20 to releasably lock the control rod in a relatively distal position with the retaining sleeve 24 thereof securely engaging the carpule 2 for a purpose that will soon be described.

A piston stem 26 is slidably received in and adapted for axial and reciprocal movement through the hollow control rod 20, such that piston stem 26 is coaxially aligned with each of the body portion 12, compression spring 14 (of FIG. 4), and control rod 20 (also of FIG. 4). Affixed to one end of piston stem 26 is a thumb ring 28, and affixed to the opposite end of stem 26 is a sharp-edged harpoon 30. As will soon be explained, the movement of piston stem 26 in a distal direction through hollow control rod 20 is manually controlled at the thumb ring 28, whereby to correspondingly advance harpoon 30 for connection to the piston 3 of carpule 2 so that said piston can be driven through the carpule for expulsing the fluid medication therefrom.

Syringe 1 is associated with a conventional double ended hypodermic needle cannula 32. Cannula 32 is affixed to a screw threaded hub 34 and is adapted to communicate with the carpule 2 at the interior of cylinder 6 by way of the carpule adapter 4. That is to say, in the assembled relationship (of FIG. 4), needle hub 34 is connected to adapter 4 via the open distal end of cylinder 6, such that one end of cannula 32 projects inwardly into the cylinder 6 to penetrate the carpule 2, and the opposite end of cannula 32 projects outwardly from the cylinder 6 to deliver the medication during the administration of an injection.

More particularly, and referring concurrently to FIGS. 1-3 of the drawings, the carpule adapter 4 includes a hollow, open ended tube-like body having a diameter which is sized to receive the medication carpule 2 therewithin. A plurality of evenly spaced, longitudinally extending tracks 38 are formed through the body of adapter 4. Located at the rearward or proximal end of each track 38 and spaced axially from one another is a stop 40 and a locking detent 42. The purpose of stops 40 and locking detents 42 will soon be described. The forward or distal end of adapter 4 includes a head portion 44 having a slightly enlarged diameter relative to the tube-like body for the dual purpose of creating a reliable snap fit of the adapter 4 within the syringe cylinder 6 while also establishing a pivot surface for permitting adapter 4 to rotate outwardly from the cylinder to achieve an important advantage that will be disclosed hereinafter when referring to FIG. 10.

A needle carrier 46 is located in and movable through the hollow interior of carpule adapter 4. Needle carrier 46 includes a generally hollow body and a plurality of radially projecting latches 48 which are received within and slidable through respective tracks 38 of adapter 4. As shown in FIG. 2, the needle carrier 46 is initially positioned forwardly in the adapter 4 and at the distal end thereof so that when the carpule 2 is inserted into the adapter, the end cap of the carpule will be received by the attached to the needle carrier. The needle carrier 46 also includes a screw threaded bore 50 which, after carpule 2 has been inserted into adapter 4 and the combination carpule and adapter have been loaded into the syringe cylinder 6 through opening 8, is adapted to be mated to the screw threaded hub 34 via the open distal end of cylinder 6. Thus, the inwardly projecting end of needle cannula 32 will extend through the bore 50 of needle carrier 46 to penetrate the carpule 2 at the interior of carpule adapter 4 (best shown in FIG. 6).

As shown in FIG. 3, when the needle carrier 46 slides rearwardly towards the proximal end of adapter 4, the latches 48 ride through tracks 38 until such latches are received in the spaces between stops 40 and locking detents 42. The latches 48 are thereby permanently retained between stops 40 and detents 42 to block any further displacement of needle carrier 46 through adapter 4 and thereby anchor said needle carrier at the proximal end of the adapter, the advantage of which will be described when referring to FIG. 11.

Referring now to FIG. 4 of the drawings, the dental syringe 1 is shown in the pre-injection state after the carpule has been inserted into and pushed forwardly through the carpule adapter 4 and the combination carpule and adapter have been loaded into the syringe cylinder 6, such that the relatively large head of adapter 4 is detachably snap-fit within the cylinder. As previously indicated, the needle carrier 46 is initially positioned at the distal end of adapter 4 to receive the end cap of the carpule 2 below the bore 50.

As was also earlier indicated, a flexible spring arm 52 is connected at one end thereof and movable with the control rod 20. Projecting radially from the opposite end of spring arm 52 is a release button 54 which is aligned and sized for receipt within a hole 58 through the body portion 12 of syringe 1 (best illustrated in FIG. 5) for the purpose of locking control rod 20 in a relatively distal relative to said body portion. However, in the pre-injection state if FIG. 4, the control rod 20 is in a proximal position relative to body portion 12, and the compression spring 14 which surrounds the control rod within body portion 12 is in a relaxed, expanded condition. Therefore, the arming flange 22 of control rod 20 is spaced axially from body portion 12, and the retaining sleeve 24 is spaced proximally from the carpule 2, such that release button 54 of spring arm 52 is positioned rearwardly of and out of engagement with the hole 18. Moreover, the piston stem 26 is located rearwardly of the control rod 20, such that the harpoon 30 thereof is also spaced rearwardly of and out of contact with the piston 3 of carpule 2.

The operation of the dental syringe 1 is now described while referring to FIGS. 5-9 of the drawings. Referring first to FIG. 5, an axially directed force is manually applied by the dentist (in the direction of the reference arrow 56) to the arming flange 22 of control rod 20, whereby to move the control rod, against the bias of compression spring 14, distally through the hollow body portion 12 of syringe 1. The flexible spring arm 52 of control rod 20 is, likewise, moved distally through body portion 12 and slightly bent therein until release button 54 pops through hole 18 to lock the control rod and thereby prevent any further displacement thereof relative to body portion 12. Accordingly, the compression spring 14 is held in a compressed state at the distal end of body portion 12. What is more, the retaining sleeve 24 of control rod 20 is also moved distally through body portion 12 and into the syringe cylinder 6 via the open proximal end thereof so as to surround and engage the proximal end of carpule 2 and thereby secure said carpule against movement relative to the cylinder.

As a preferred embodiment of the present invention, and referring concurrently to FIGS. 5 and 5′, a ring-shaped elastomeric (e.g. rubber) liner 58 extends around the interior periphery of the retaining sleeve 24 of control rod 20. The liner 58 includes a series of evenly spaced, radially inward extending projections 60 which establish a tight friction fit against the carpule 2 when the retaining sleeve 24 is advanced through the body 12 of syringe 1 to surround and engage the proximal end of said carpule. In this manner, the projections 60 of liner 58 may be slightly compressed to permit retaining sleeve 24 to firmly grasp carpule 22 and thereby assure that a subsequent rearward relocation of the control rod 20 through body portion 12 will cause a corresponding rearward relocation of the carpule 2 through cylinder 6 (in a manner to be described when referring hereinafter to FIG. 8).

FIGS. 6 and 7 of the drawings illustrate the dental syringe in the injection state. More particularly, and referring to FIG. 6, with the control rod 20 advanced to and locked at a relatively distal position and the carpule 2 secured within the syringe cylinder 6 by retaining sleeve 24, the dentist applies an axial force (in the direction of the reference arrow 64) to the thumb ring 28 of piston stem 26 to advance stem 26 distally through the hollow control rod 20 until the harpoon 30 penetrates the piston 3 of carpule 2 at the proximal end of cylinder 6. Accordingly, a piston assembly is formed comprising the interconnection of piston stem 26 to piston 3. Next, a conventional double ended hypodermic needle 32, which is affixed to and supported by a conventional screw threaded hub 34, is interfaced with carpule 2 via the open distal end of cylinder 6. More particularly, the screw threaded hub 34 is mated to the screw threaded bore 50 of needle carrier 46 at the distal end of carpule adapter 4, such that the inwardly projecting end of cannula 32 penetrates the carpule to communicate the fluid contents thereof, and the outwardly projecting end of cannula 32 extends outside the cylinder 6 for administering an injection of said contents.

In FIG. 7, an injection is administered by syringe 1 in a medically accepted fashion. That is to say, the dentist first locates the outwardly projecting end of needle cannula 32 at a targeted tissue area of the patient. The dentist then resumes the application of the axial force to the thumb ring 28 of piston stem 26, whereby to continue the distal displacement of piston stem 26 through hollow control rod 20 for correspondingly driving the piston 3 through the carpule 2. The distal relocation of piston 3 through the carpule 2 expulses a suitable volume of fluid medication to the patient via the needle cannula 32.

FIGS. 8 and 9 show the dental syringe in the post-injection state after an injection has been either partially (in FIG. 8) or fully (in FIG. 9) administered and the needle cannula has been removed from the patient'tissue. In FIG. 8, the needle cannula 32 is shown temporarily retracted within the syringe cylinder 6 to avoid an accidental needle stick prior to a resumption and completion of the injection. By way of example, it may be desirable to retract cannula 32 temporarily if the dentist wishes to momentarily lay the syringe in a dental tray and thereby administer the injection incrementally in two or more successive steps. In this case, the dentist depresses the release bottom (shown in phantom and designated 54-1) against the bias of spring arm 52 to move the button inwardly of its hole 18 and thereby bend spring arm 52 in a radially inward direction. The depression of release button 52 through hole 18 unlocks the control rod 20 from its distally advanced position relative to the body portion 12 of syringe 1. The compression spring 14 is now free to return to its normal, expanded state, such that the stored potential energy within spring 14 will automatically and simultaneously drive control rod 20 and piston stem 26 in a proximal direction (as indicated by the reference arrow 66) through body portion 12. The proximal movement of control rod 20 and piston stem 26 correspondingly causes the carpule 2 to be relocated proximally through cylinder 6 for receipt within body portion 12 (via the open proximal end of the cylinder), whereby cannula 32 is safely retracted into the cylinder 6.

When the dentist later wishes to complete the injection, he once again applies an axial force to the arming flange 22 of control rod 20 to advance the control rod 20 and piston stem 26 distally through body portion 12 to return carpule 2 and cannula 32 to the injection state of FIG. 7. The piston 3 is then driven through the carpule 2 by means of piston stem 26 to expulse all (or another portion) of the remaining fluid medication. Of course, if all of the fluid were to be initially expulsed from carpule 2 during a single, continuous step, such that the temporary retraction of cannula 32 into cylinder 6 would not be needed, then the post-injection steps described with reference to FIG. 8 may be avoided.

In FIG. 9, the injection has now been completed so that the needle cannula 32 can be safely and permanently retracted into the carpule adapter 4. More particularly, the dentist uses his thumb and forefinger to grasp the proximal end of carpule 2 (by way of the opposing opening 8 and window 10 through the cylinder 6) to thereby prevent the relocation of the carpule relative to the cylinder. Next, the dentist depresses the release buttom 54, whereby to move the button inwardly and against the bias of spring arm 52 through the hole 18 to unlock the control rod 20 from its distally advanced position and permit compression spring 14 to return to the expanded state (in the manner described while referring to FIG. 8).

While maintaining a firm grasp on carpule 2 with one hand, the dentist uses his opposite hand to grasp and pull the arming flange 22 of control rod 20 in a reward direction (as indicated by the reference arrow 68). Pulling the arming flange 22 in a reward direction correspondingly causes the control rod 20 and the retaining sleeve 24 thereof to be relocated proximally through the hollow body portion 12 of syringe 1. Therefore, the retaining sleeve 24 which previously surrounded and engaged the proximal end of the carpule 4 is now disengaged from said carpule to permit the carpule to be displaced relative to the syringe cylinder 6. The proximal relocation of the control rod 20 also displaces piston stem 26, whereby to detach the harpoon 30 from piston 3. The piston stem 26 may then be withdrawn from the carpule 2 by means of pulling the finger ring 28 in a rearward position.

Figure 12:
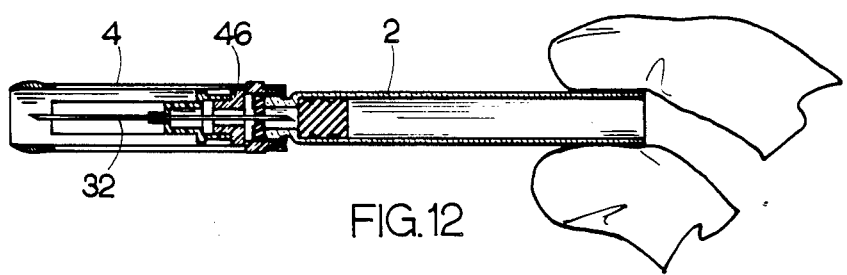

FIGS. 10 and 12 of the drawings illustrate the removal of the combination carpule 2 and adapter 4 from the syringe cylinder 6 and the retraction of the needle cannula 32 into the adapter. In FIG. 10, after the control rod 10 and piston stem 26 have been relocated proximally through the hollow body portion 12 of syringe 1, whereby carpule 2 can be displaced relative to the cylinder, the syringe 1 is turned so that the opening 8 through cylinder 6 faces downwardly. The combination carpule 2 and carpule adapter 4 are pivotally supported within cylinder 6 at the enlarged head 44 of adapter 4 so as to rotate, under the influence of gravity, downwardly and outwardly from the cylinder via the opening 8 therethrough.

Figure 11:
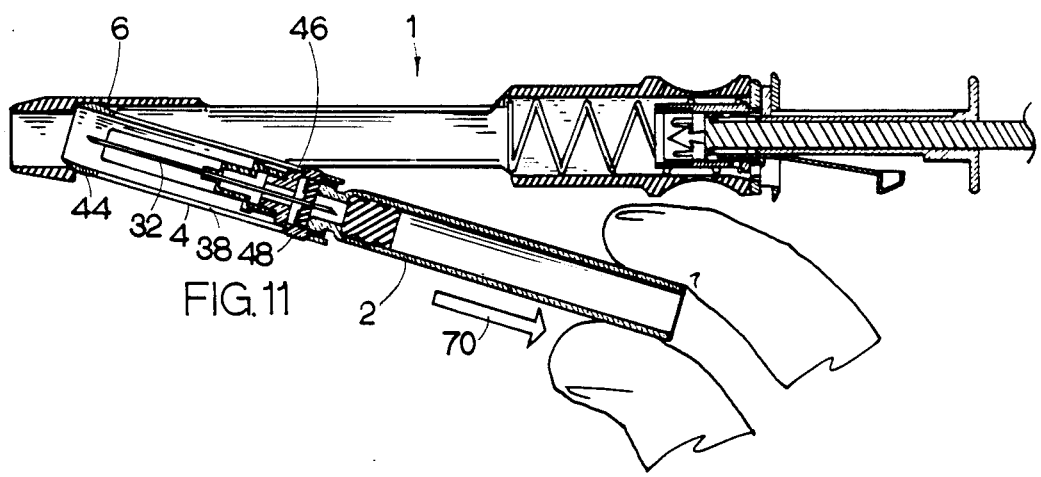

In FIG. 11, with the carpule adapter 4 still pivotally supported within cylinder 6 at the enlarged head 44 of the adapter, the dentist grasps the carpule 2 and applies a proximal pulling force thereto (in the direction indicated by the reference arrow 70). Accordingly, the carpule 2 and needle carrier 46 attached thereto slide proximally through adapter 4, such that the latches 48 of carrier 46 ride through respective longitudinally extending tracks 38 in adapter 4 until each latch 48 is seated in the space between a stop and a locking detent (designated 40 and 42 and best shown in FIG. 3) to prevent any further displacement of needle carrier 46. The needle carrier 46 is thereby anchored at the proximal end of adapter 4 with the needle cannula retracted completely within and surrounded by said adapter.

In FIG. 12, the dentist continues to apply a proximal pulling force to carpule 2 until the carpule adapter is separated from its pivotal attachment to the syringe cylinder 6. Accordingly, a compact disposal package is now available consisting of the empty carpule 2 pulled rearwardly through and locked (by means of anchoring the needle carrier 46) within the carpule adapter 4. What is more, the needle cannula 32 is irretrievably located within adapter 4 so as to be rendered inaccessible and non-reusable. Therefore, the disposal package may be safely handled and discarded while avoiding the possibility of an accidental needle stick and the threat of spreading a contagious, and conceivably life threatening, disease. The dental syringe 1 of the present invention is then ready for sterilization and reuse with a fresh medication filled carpule, carpule adapter, and needle cannula in the manner that has been described above.

It will be apparent that while a preferred embodiment of the invention has been shown and described, various modifications and changes may be made without departing from the true spirit and scope of the invention. For example, although the syringe 1 has been described as having particular application as a dental syringe, it is to be understood that this is not to be regarded as a limitation of the claimed invention. That is, the syringe 1 is also adapted for any other use where a fluid is to be injected from a prefilled carpule.

Having thus set forth a preferred embodiment of the present invention, what is claimed is:

1. A syringe including a hollow syringe cylinder having an open distal end and comprising:
    a fluid filled carpule;
    a hollow carpule adapter having forward and rearward ends and a needle carrier located at the forward end of and movable through said adapter, said carpule adapter receiving at least some of said carpule therewithin and said needle carrier having means to engage said carpule at the forward end of said adapter, said syringe cylinder being sized so that said combination carpule and carpule adapter can be loaded therein;
    a double ended needle cannula to be attached to the needle carrier of said carpule adapter such that one end of said cannula penetrates said carpule and the opposite end of said cannula projects through the open distal end of said syringe cylinder for injecting the fluid contents of said carpule; and
    means for moving said carpule towards the rearward end of said carpule adapter for correspondingly relocating said needle carrier and retracting said cannula rearwardly within said carpule adapter so as to be surrounded and shielded to thereby avoid an accidental needle stick.

2. The syringe recited in claim 1, wherein said carpule adapter has at least one locking detent located adjacent the rearward end thereof so as to engage the anchor said needle carrier when said carpule is moved towards the rearward end of said adapter, the anchoring of said needle carrier preventing a displacement of said needle cannula out of its retracted position.

3. The syringe recited in claim 2, wherein said needle carrier has at least one latch extending therefrom to be engaged by the at least one locking detent of said carpule adapter to anchor said needle carrier when said carpule is moved towards the rearward end of said adapter.

4. The syringe recited in claim 3, wherein said carpule adapter has at least one longitudinally extending track, said locking detent being formed in said track at the rearward end of said adapter, the latch of said needle carrier riding through the track of said carpule adapter to be engaged by said locking detent for anchoring said needle carrier when said carpule is moved towards the rearward end of said adapter.

5. The syringe recited in claim 1, wherein said syringe cylinder has a longitudinally extending opening formed therein through which to load said combination carpule adapter and carpule, the forward end of said carpule adapter having a relative large head, such that said carpule adapter can be pivotally and releasably attached to said cylinder through said longitudinally extending opening.

6. The syringe recited in claim 5, wherein the means for moving said carpule towards the rearward end of said carpule adapter is an axial pulling force applied to said carpule so as to cause said carpule to slide rearwardly through said adapter after said adapter has been pivoted at the large head thereof and said carpule has been rotated out of said syringe cylinder through the longitudinally extending opening therein.

7. A syringe including a hollow syringe body and a hollow syringe cylinder each of said body and said cylinder being axially aligned with one another and having open proximal and distal ends, said syringe comprising;
   a fluid filled carpule to be loaded into said cylinder, said carpule having a piston located at a proximal end thereof and movable through said carpule for expulsing the fluid contents thereof;
   a double ended needle cannula to be interconnected with said carpule so that one end of said cannula penetrates said carpule and the other end of said cannula projects outwardly through the distal end of said cylinder for injecting the fluid of said carpule;
   a piston stem movable axially through said syringe body to be connected to the piston of said carpule for controlling the movement of said piston through said carpule;
   a control rod advanceable distally through said syringe body and into said cylinder and having a retaining sleeve at one end thereof for surrounding and engaging the proximal end of said carpule to prevent the relocation of said carpule through said cylinder;
   catch means extending outwardly from and being movable with said control rod through said syringe body; and
   locking means associated with said syringe body for releasably engaging the catch means of said control rod a said control rod moves distally through said syringe body for locking said control rod at its distally advanced position and maintaining the retaining sleeve of said control rod in engagement with said carpule.

8. The syringe recited in claim 7, wherein said control rod is hollow and said piston stem is received in and slidable through said control rod.

9. The syringe recited in claim 7, wherein said catch means is a flexible spring arm attached at one end thereof to said control rod and having a release button extending from the opposite end.

10. The syringe recited in claim 9, wherein said looking means is a hole formed through said syringe body and aligned to removably receive the release button of said spring arm as said control rod moves distally through said syringe body, said release button being movable out of said hole against the normal bias of said spring arm to release the control rod from its distally advanced position.

11. The syringe recited in claim 7, further comprising a compression spring surrounding said control rod at the interior of said hollow syringe body, said spring being compressed against its normal spring bias when said control rod is moved to and locked in its distally advanced position, said compression spring expanding under its normal bias when the locking means of said syringe body releases the catch means of said control rod, such that said control rod is released from the distally advanced position and driven proximally through said syringe body to relocate said carpule proximally through said syringe cylinder and thereby retract said needle cannula into said cylinder through the open distal end thereof.

12. The syringe recited in claim 7, wherein the retaining sleeve of said control rod has an elastomeric liner extending around the inner periphery thereof to establish a reliable engagement of said carpule by said retaining sleeve.

13. The syringe recited in claim 7, further comprising a hollow carpule adapter having open forward and rearward ends, said carpule being received forwardly in and slidable axially through said carpule adapter, such that said combination carpule and adapter are loaded into said syringe cylinder,
   the locking means of said syringe body releasing the catch means of said control rod to release said control rod from its distally advanced position and allow said control rod to be relocated proximally through said syringe body and the retaining sleeve of said control rod to be moved out of engagement with said carpule, whereby said carpule is slidable rearwardly through said carpule adapter to retract said needed cannula completely within said adapter.

14. The syringe recited in claim 13, further comprising means for anchoring said carpule at a relatively rearward position within said carpule adapter to prevent the return movement of said carpule forwardly through said adapter.

15. The syringe recited in claim 13, wherein said carpule adapter has a relatively large head to be pivotally attached to said syringe cylinder, said cylinder having a longitudinally extending opening through which said adapter may pivot to rotate said carpule outwardly from said cylinder so that said carpule can slide rearwardly through said adapter.

16. A syringe including a hollow syringe body and a hollow syringe cylinder, each of said body and said cylinder being axially aligned with one another and having open proximal and distal ends, said syringe comprising:
   a fluid filled carpule having a piston movable therethrough for expulsing the fluid contents thereof;
   a double ended needle cannula to be interconnected with said carpule so that one end of said cannula penetrates said carpule and the other end of said cannula projects outwardly through the open distal end of said cylinder for injecting the fluid of said carpule;
   a piston stem movable axially through said syringe body and into said cylinder to be connected to the piston of said carpule for controlling the movement of said piston through said carpule;
   a hollow control rod for receiving said piston stem therethrough, said control rod advanceable distally through said syringe body and into said cylinder and having a retaining sleeve at one end for surrounding and engaging the proximal end of said carpule to prevent the relocation of said carpule through said cylinder;

a flexible spring arm attached at one end thereof to said control rod and having a release button extending from the opposite end, said spring arm being movable with said control rod through said syringe body;

a hole formed through said syringe body to removably receive the release button of said spring arm as said control rod moves distally through said syringe body for locking said control rod at its distally advanced position and maintaining the retaining sleeve of said control rod in engagement with said carpule; and compression spring means surrounding said control rod at the interior of said hollow syringe body, said spring means compressed against the normal spring bias when said control rod is moved to and locked at its distally advanced position, said compression spring means expanding when the release button of said spring arm is removed from the hole in said syringe body to release said control rod from its distally advanced position and drive said control rod proximally through said syringe cylinder and thereby retract said needle cannula into said cylinder through the open distal end thereof.

* * * * *